United States Patent
Rosing et al.

[11] Patent Number: 5,863,896
[45] Date of Patent: Jan. 26, 1999

[54] EVALUATION OF SUBSTANCES FOR ALTERING AND FOR INCREASING APC RESPONSE

[75] Inventors: Jan Rosing, Valkenburg; Guido Tans, Maastricht, both of Netherlands; Katalin Varadi; Hans Peter Schwarz, both of Vienna, Austria

[73] Assignee: Immuno AG, Vienna, Austria

[21] Appl. No.: 555,423

[22] Filed: Nov. 9, 1995

[51] Int. Cl.$^6$ .......................... A01N 37/18; A61K 38/00; A61K 35/14; C12Q 1/56
[52] U.S. Cl. ...................... 514/12; 514/8; 514/2; 435/13; 435/69.2; 435/69.6; 436/69; 530/380; 530/381; 530/383; 530/384; 424/530
[58] Field of Search ...................... 514/2, 8, 12; 435/13, 435/4, 69.2, 69.6; 424/530; 436/69; 530/380–384

[56] References Cited

U.S. PATENT DOCUMENTS

| | | | |
|---|---|---|---|
| 4,640,834 | 2/1987 | Eibl et al. | 424/94 |
| 5,254,532 | 10/1993 | Schwarz et al. | 514/2 |

FOREIGN PATENT DOCUMENTS

| | | |
|---|---|---|
| 0519903A1 | 12/1992 | European Pat. Off. |
| 0656424A2 | 6/1995 | European Pat. Off. |
| WO 95/01433 | 1/1995 | WIPO |

OTHER PUBLICATIONS

Thrombosis and Haemostasis, 62: 25, Abstract No. 37 (1989).
Amer et al., Thrombosis Research 57: 247–258 (1990).
Greengard et al., The Lancet 343: 1361–1362 (May 28, 1994).
Martinoli et al., Thrombosis Research 43: 253–264 (1986).
Nicolaes et al., J. Biological Chemistry 270(36): 21158–21166 (Sep. 8, 1995).
Camire et al., J. Biological Chemistry 270(35): 20794–20800 (Sep. 1, 1995).
Suzuki et al., Biochem 96: 455–460 (1984).
Schwarz et al., Blood 64(6): 1297–1300 (Dec. 1984).
Kalafatis et al., J. Biological Chemistry 270(8): 4053–4057 (Feb. 24, 1995).
Kalafatis et al., J. Biological Chemistry 269(50): 31869–31880 (Dec. 16, 1994).
Walker et al., Biochimica Et Biophysica Acta 517: 333–342 (1979).
Jenny et al., Proc. Natl. Acad. Sci. USA 84: 4846–4850 (Jul. 1987).
Suzuki et al., J. Biological Chemistry 257(11): 6556–6564 (Jun. 10, 1982).
Voorberg et al., The Lancet 343:1535–1536 (Jun. 18, 1994).
Saragovi et al., Science 253: 792–795 (Aug. 1991).
Taylor et al., J. Clin. Invest. 79: 918–925 (Mar. 1987).
Tans et al., Blood 77(12): 2641–2648 (Jun. 15, 1991).
Dreyfus et al., New England Journal of Medicine 325: 1565–1568 (Nov. 28, 1991).
Griffin et al., J. Clin. Invest., 68: 1370–1373 (Nov. 1981).
Bertina et al., Nature 369: 64–67 (May 5, 1994).
Koster et al., Lancet 342: 1503–1506 (Dec. 1993).
Dahlback et al., Proc. Natl. Acad. Sci. USA 90: 1004–1008 (Feb. 1993).
Walker, J. Biological Chemistry 256(21): 11128–11131 (1981).
Comp et al., Clin. Invest. 74(6): 2082–2088 (1984).
Kalafatis et al., J. Biological Chemistry 269(50): 31869–31880 (Dec. 16, 1994).
Solymoss et al., J. Biological Chemistry 263(29): 14884–14890 (Oct. 15, 1988).
Walker, J. Biological Chemistry 255(12): 5521–5524 (Jun. 25, 1980).
Suzuki et al., J. Biological Chemistry 258(3): 1914–1920 (Feb. 10, 1983).
Gruber et al., Blood 73(3): 639–642 (Feb. 15, 1989).
Rosing et al., J. Biological Chemistry 268(28): 21130–21136 (Oct. 5, 1993).
Esmon, J. Biological Chemistry 264(9): 4743–4746 (Mar. 25, 1989).

*Primary Examiner*—Robert A. Wax
*Assistant Examiner*—Tekchand Saidha
*Attorney, Agent, or Firm*—Foley & Lardner

[57] ABSTRACT

The present invention provides methods, reagents, and test kits for evaluating the effect of a test composition on APC response by employing factor Va$^{R506Q}$. Methods and compositions for treating patients suffering from reduced APC response are also provided.

21 Claims, 1 Drawing Sheet

EVALUATION OF SUBSTANCES FOR ALTERING AND FOR INCREASING APC RESPONSE

BACKGROUND OF THE INVENTION

The present invention relates to a method, reagent and test kit for evaluating substances that alter APC response. The invention further relates to a method and a composition for treating a patient with abnormal APC response.

Protein C is the zymogen form of a serine protease known as activated protein C ("APC"), which is a vitamin K-dependent plasma glycoprotein that has anticoagulant and profibrinolytic properties in vivo and in vitro. See, e.g., Esmon, *J. Biol. Chem.* 264: 4743–46 (1989). Protein C can be activated by the thrombin-thrombomodulin complex on endothelial surfaces.

The anticoagulant effect of APC is the result of proteolytic degradation of both activated factor V ("factor Va"), the cofactor for factor IXa-mediated prothrombin activation, and activated factor VIII ("factor VIIIa"), the cofactor for factor IXa-mediated activation of factor X.

The action of APC can lead to the interruption of thrombin generation and the prevention of activation of the coagulation system. Inhibition of thrombin formation by APC can prevent consequences of (local) thrombin generation such as activation, adhesion and aggregation of platelets; release of vasoactive and proinflammatory material; increase in endothelial permeability; expression of platelet activating factor and granule membrane protein-140 on endothelial cells.

Because the microcirculation is the major site of function of the protein C pathway, the adverse effects of severe protein C deficiency typically first become manifest in the capillaries of the skin, and then progress to the vessels of the eyes, brain and kidneys. Protein C deficiency can result in capillary thrombosis and interstitial bleeding. For example, the protein C deficiency can cause ecchymotic skin lesions which, if untreated, rapidly develop into hemorrhagic bullae with subsequent gangrenous necrosis, sometimes extending to the fascia and leading to autoamputation.

The physiological importance of the protein C pathway is further demonstrated by the occurrence of life-threatening purpura fulminans as a result of excess thrombin formation in homozygous protein C-deficient infants, Dreyfus et al., *N. Eng. J. Med.* 325: 1565–68 (1991), and by the increased risk of thrombotic events in patients with heterozygous protein C deficiency. Griffin et al., *J. Clin. Invest.* 68: 1370–73 (1981). Infusion of highly purified APC into animals can prevent arterial or venous thrombus formation in various experimental models, see Gruber et al., *Blood,* 73: 639–42 (1989), and Schwarz et al., *Thromb. Haemostas.,* 62: 25 (1989), and can prevent *E. coli*-induced death in a baboon model of sepsis. Taylor et al., *J. Clin. Invest.* 79: 918–25 (1987).

As described above, one function of APC is to inactivate factor Va. Human blood coagulation factor Va is a heterodimeric glycoprotein that includes a heavy chain (molecular weight of about 105,000 daltons) and a light chain (about 72,000–74,000 daltons). Suzuki et al., *J. Biol. Chem.* 257: 6556–6564 (1982); Rosing et al.,*J. Biol. Chem.* 268: 21130–21136 (1993). The heavy and light chains are non-covalently associated together by divalent metal ions, such as $Ca^{2+}$. The heavy chain region (amino acids 1–709) is composed of two A domains (A1 and A2) associated with a connecting region (amino acids 304–316). The light chain region of the factor (amino acids 1546–2196) includes one A and two C domains (A3, C1, C2). The amino acid sequence of human factor V is described by Jenny et al., *Proc. Nat'l Acad. Sci. USA* 84: 4846–50 (1987).

The heavy and light chain regions are connected in factor V through the connecting B region, which is removed during activation to form factor Va. Factor Va is a cofactor of activated factor X (factor Xa), that drastically (more than 1000 fold) accelerates the factor Xa catalyzed formation of thrombin from prothrombin.

Proteolytic inactivation of factor Va by APC is one of the key reactions in the regulation (limitation) of thrombin formation. APC-catalyzed cleavage of factor Va is stimulated by the presence of negatively charged membrane surfaces and by protein S. Walker et al., *Biochim. Biophys. Acta* 571: 333–342 (1979); Suzuki et al.,*J. Biol. Chem.* 258: 1914–1920 (1983); Bakker et al., *Eur. J. Biochem.* 208: 171–178 (1992); Walker, *J. Biol. Chem.* 255: 5521–5524 (1980); Solymoss et al., *J. Biol. Chem.* 263: 14884–14890 (1988). The loss of cofactor activity by factor Va is associated with peptide bond cleavages in its heavy chain at $Arg^{306}$, $Arg^{506}$, and $Arg^{679}$. Kalafatis et al., *J. Biol. Chem.* 269: 31869–80 (1994), Kalafatis et al., *loc. cit.* 270: 4054–57 (1995). The physiologic importance of the down-regulation of factor Va activity by APC is underscored by the observation of recurrent thromboembolic events in individuals that are deficient in either protein C or protein S. Griffin et al., *J. Clin. Invest.* 68: 1370–1373 (1981), Schwarz et al., *Blood* 64: 1297–1300 (1984), Comp et al., *J. Clin. Invest.* 74: 2082–2088 (1984).

There have been reports that cleavage at $Arg^{506}$ alone in normal factor Va has no effect on cofactor activity. However, this cleavage has previously been thought to be necessary for efficient exposure of cleavage sites at $Arg^{306}$ and $Arg^{679}$, which are associated with cofactor inactivation. $Arg^{306}$ is in the A1 region, $Arg^{506}$ is in the A2 region and $Arg^{679}$ is in a small part of the B-domain that remains in the heavy chain of factor Va after activation of factor V. In the absence of a membrane surface, APC cleaves factor Va heavy chain to generate a fragment of 75 kD, as well as 28/26 kD and 22/20 kD doublets. Further fragmentation of the heavy chain is possible only in the presence of phospholipids from membrane surfaces. In the presence of such surfaces, APC quickly inactivates factor Va.

There have been recent studies of APC-catalyzed inactivation of factor Va and factor $va^{R506Q}$ (a mutant where glutamine replaces arginine at position 506) in the presence and absence of phospholipid vesicles, Nicolaes et al.,*J. Biol. Chem.* 270: 21158–66 (1995), or platelet membranes. Camire et al., *J. Biol. Chem.* 270: 20794–800 (1995). These studies suggest that cleavage of the peptide bond at $Arg^{306}$ of factor Va occurs in the absence of phospholipids and that this cleavage is not significantly affected by precleavage of the peptide bond at $Arg^{506}$, Accordingly, the cleavage at $Arg^{306}$ does not require exposure through binding of factor Va to membranes or cleavage of the molecule at $Arg^{506}$.

Suzuki et al., *J. Biochem.* 96: 455–60 (1984) found that factor Va was inactivated by APC in a purified system depending on the presence of cofactor protein S. Platelet-associated factor Va was incubated with APC and protein S, whereby the rate of factor Va inactivation was about 25 fold higher than without protein S. This stimulating effect of protein S was only minor when thrombin-modified protein S was used as a cofactor for APC. Therefore, this modified protein S was considered to be inefficient. Additionally, an extensive study of the effect of protein S on APC-catalyzed inactivation of platelet factor Va showed only marginal stimulation by protein S. Tans et al., *Blood* 77: 2641–48 (1991).

In the art, protein S appeared to be a rather poor stimulator of the physiological APC catalyzed factor Va inactivation.

Bakker et al., *Eur. J. Biochem.* 208: 171–78 (1992). The protein S dependent rate enhancement was observed only in reaction mixtures that contained negatively charged phospholipid vesicles. The effect is dependent upon the assay conditions, such as the phospholipid source. It was suggested that in the human system enhancement of APC binding to phospholipid vesicles by protein S is of minor importance. The mechanism of action of protein S in factor Va inactivation is, however, not fully understood.

The anticoagulant effect of APC in vitro is reflected by the fact that APC results in a dose-dependent prolongation of clotting time in assays based on factor Xa or activated partial thromboplastin time (aPTT), provided that a cofactor, the vitamin K-dependent protein S, is present. Walker, *J. Biol. Chem.* 256: 11128–31 (1981). Amer and Kisiel have observed that the addition of APC to plasma from a patient with thrombosis did not result in the expected prolongation of clotting time. Amer et al., *Thrombos. Res.*, 57: 247–58 (1990). Dahlbäck demonstrated that the addition of APC to plasma from certain patients with thrombosis but no deficiency of the main inhibitors of clotting (such as antithrombin III, protein C and protein S) did not result in prolongation of the aPTT and suggested a new concept of the pathogenesis of hereditary thrombophilia, referred to as "APC resistance." Dahlbäck et al., *Proc. Nat'l Acad. Sci. USA* 90: 1004–08 (1993).

Several laboratories have associated the occurrence of familial thrombophilia in a large group of patients with a poor anticoagulant response to APC (APC resistance or reduced APC response). Dahlbäck et al. supra. Those patients suffer from thrombotic events despite of having protein S level in a normal range. APC resistance is at least 10 times more common than all other known genetic thrombosis risk factors together and has an allelic frequency of about 2% in the Dutch population. Koster et al., *Lancet* 342: 1503–1506 (1993). A molecular defect in APC-resistant patients was recently demonstrated to be linked to a single point mutation in the factor V gene that causes an amino acid substitution of Gln for Arg at position 506 ("factor $V^{R506Q}$"), which is a position where cleavage occurs during APC-catalyzed inactivation of native factor Va. Bertina et al., *Nature* 369: 64–67 (1994); Greengard et al., *Lancet* 343: 1361–62 (1994); Voorberg et al., *Lancet* 343: 1535–36 (1994); Kalafatis et al., *J. Biol. Chem.* 269: 31869–80 (1994).

The phrase "APC response" refers to the functional defect of patients who do not respond to the activity of APC in an appropriate way. An extreme case of reduced APC response is APC resistance, which often occurs in patients who are homozygous for a factor V mutation. The APC response therefore may be determined via a functional test such as aPTT in the presence of APC, or a coagulation assay for inactivating factor VIII by APC, which could be designed as a chromogenic assay. See, for example, the determination of sensitivity to APC which is described in published European application No. 65 64 24.

Because of the necessity to treat APC response disorders, there exists a need for methods, reagents and test kits to evaluate the properties of compositions to treat APC response disorders, as well as therapeutic compositions themselves. These needs are satisfied by the present invention.

SUMMARY OF THE INVENTION

It is an object of the present invention to provide a method for evaluating the effects of a test composition on APC response.

It is another object of the present invention to provide a reagent and test kit for evaluating the effects of a test composition on APC response.

It is still another object of the invention to provide a composition and method for treating a patient suffering from a reduced APC response using protein S.

In accordance with one aspect of the present invention, there is provided a method for evaluating the effect of a test composition on APC response, comprising the steps of (a) incubating the test composition with factor $Va^{R506Q}$ and APC; (b) determining a level of factor $Va^{R506Q}$ inactivation in the presence of the test preparation; and (c) comparing the level of step (b) with a level of factor $Va^{R506Q}$ inactivation obtained in the absence of the test composition in order to evaluate said effect of said test composition. Factor $Va^{R506Q}$ can be obtained from plasma or a plasma fraction, or by recombinant DNA technology. Preferably, the test composition also is contacted with calcium ions and phospholipids.

Typically, the test composition is a pharmaceutical preparation containing protein S or a mutant of protein S, or another type of compound that is believed to increase the APC response. When a plasma sample of a patient is to be analyzed for the content of functionally active protein S, the test composition can be a plasma sample. Additionally, the invention also can be used to determine whether a test composition would interfere or inhibit the APC response.

Preferably, the incubating step is performed at a temperature of about 15° C.–37° C. for about 5–30 minutes, and the determining step is based upon measuring the amount or kinetics of active factor $Va^{R506Q}$ remaining after and during the incubating step. Residual active factor $Va^{R506Q}$ can be determined based upon cofactor activity for prothrombin activation. Thrombin generation can be detected with a chromogenic substrate or other known means.

In accordance with another aspect of the present invention, there are provided reagents and test kits for evaluating the effect of a test composition on APC response. The reagents and test kits comprise factor $Va^{R506Q}$ and APC, and preferably calcium ions and phospholipids. Preferably, the reagent and test kit do not contain protein S. However, if the test compositions are not protein S preparations, protein S can be included in the reagent and test kit according to the invention. The test kit according to the present invention can contain protein C and an activator of protein C instead of APC.

In accordance with still another aspect of the present invention, there is provided a method of treating a patient suffering from a reduced APC response, including APC resistance, comprising the step of administering protein S or a mutant of protein S to the patient. Preferably, the patient to be treated is homozygous for a factor Va mutation.

In accordance with yet another aspect of the present invention, there is provided a composition for treating patients with reduced APC response, including APC resistance, comprising protein S or a mutant of protein S in a pharmaceutically acceptable carrier.

These and other aspects of the present invention will become apparent to the skilled artisan in view of the disclosure contained herein. Modifications may be made to the various teachings of this invention without departing from the scope and spirit of the invention.

DETAILED DESCRIPTION OF PREFERRED EMBODIMENTS

Figure 1:
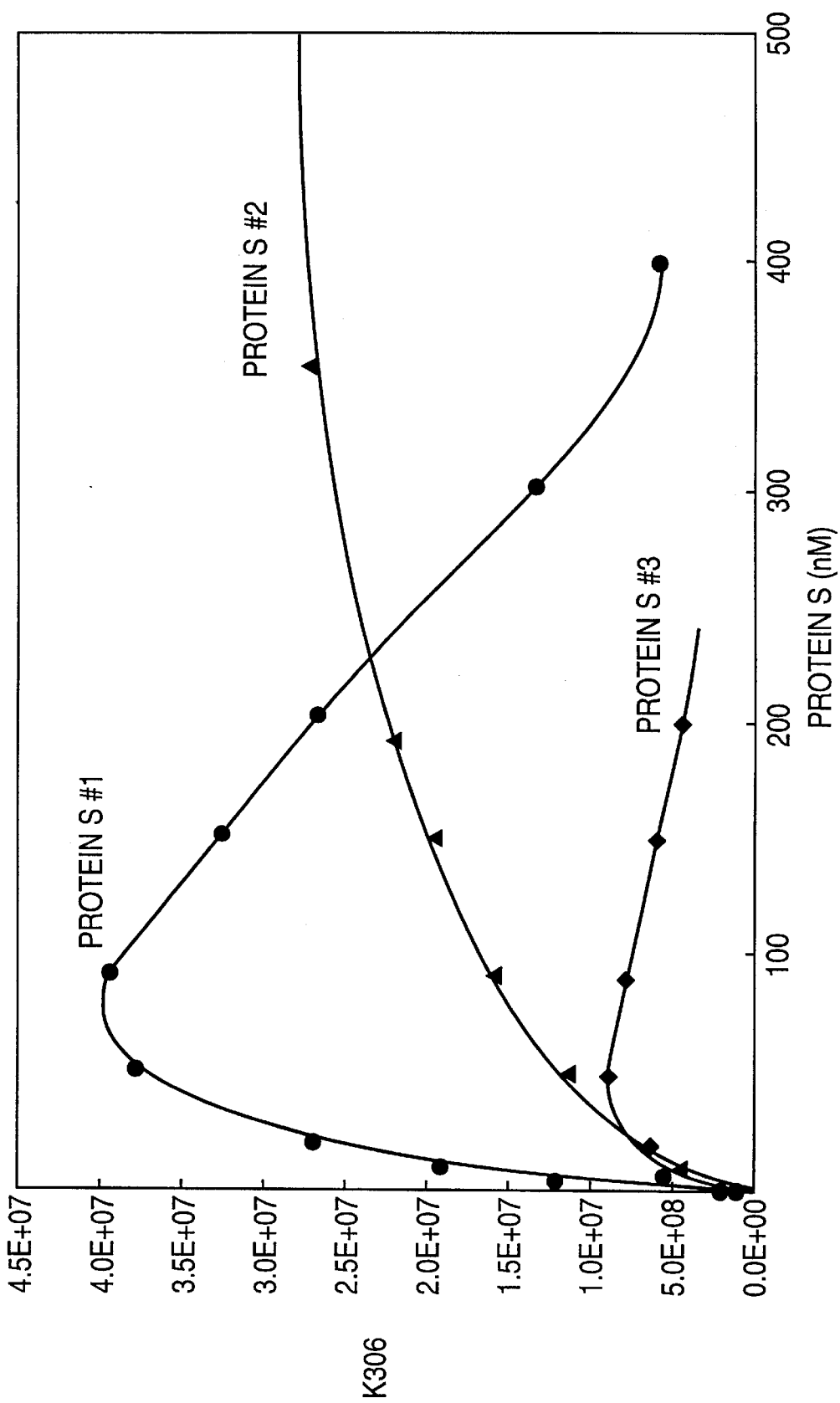
FIG. 1 depicts data concerning the effect of different protein S preparations on APC catalyzed inactivation of factor $Va^{R506Q}$.

The present invention provides a method, reagent and test kit employing factor Va$^{R506}$ to evaluate the ability of a test composition to alter an APC response. The Va$^{R506Q}$ may be isolated by conventional means from serum or plasma of a patient being heterozygous or homozygous for the factor Va$^{R506Q}$ mutation, or it may be obtained from a cell culture expressing the protein. Additionally, any mutant or factor V and/or factor VIII that contributes to the phenomenon of abnormal APC response may be used as an alternative or in addition to factor Va$^{R506Q}$.

Preferably, the reagent employed according to the invention does not contain substantial amounts of protein S, which increases APC response, in order to obtain an unambiguous result that is not influenced by contaminating protein S. Surprisingly, factor Xa does not interfere with the method according to the invention, and factor Xa therefore is not critical to work under purified conditions. Accordingly, factor X or factor Xa can be present.

APC itself can be used according to the present invention. Preferably, APC is used in a highly purified form, that is, with a purity of more than 90%. Alternatively, protein C and an activator of protein C can be provided in order to obtain the APC employed according to the invention. The activator of APC should be a physiological enzyme or a trypsin or trypsin-like enzyme. The activator should be capable of activating protein C without interfering with the inactivation of factor Va by APC. Preferred activators include thrombin/thrombomodulin and snake venoms, such as Protac C®. Martinoli et al., *Thromb. Res.* 43: 253–64 (1986).

Phospholipids also can be used according to the invention. These phospholipids may be selected from a fraction containing platelets or chemically pure phospholipids. It is preferred to use negatively charged phospholipids. It also is preferred to provide the phospholipids in a vesicle form. The most preferred embodiment comprises the use of a mixture of dioleoylphosphalidylserine and dioleoylphosphalidylcholine ("DOPS/DOPC", 10/90, M/M), which is available from commercial sources such as Avanti Polar Lipids.

The test composition should be incubated in the presence of a test composition at a temperature of 15° C.–37° C. for a period of 5–30 minutes. Depending on the efficacy of the test substance, APC is reacting with the factor Va mutant during this period. After the incubation is stopped by dilution or by a suitable inhibitor, the residual factor Va activity is measured as a cofactor activity for thrombin generation. This determination step is usually carried out by means of the conversion of a chromogenic substrate specific for thrombin activity, such as S2238 (Chromogenix). It is also useful to employ a coagulation assay, where the coagulation time is determined. It is however preferred to employ a factor Va assay according to Tans et al., *Blood* 77: 2641–48 (1991).

A wide concentration range of components can be used: phospholipids (5–100 μM, preferable 10–50 μM), calcium ions (1–50 mM, preferable 2–5 mM), factor Va$^{R506Q}$ (0.01–20 nM, preferable 0.01–5 nM) and APC (0.01–2 nM, preferable 0.05–0.5 nM).

Based on kinetic data analysis the effect of protein S on the APC catalyzed inactivation of factor Va was investigated. It turned out that protein S preferentially accelerates the slow phase of factor Va inactivation, which means protein S promotes the cleavage at Arg$^{303}$. Surprisingly, protein S does not effect cleavage at Arg$^{506}$ but promotes further processing of the reaction intermediate by accelerating cleavage at Arg$^{306}$.

The kinetic studies confirm that APC-catalyzed inactivation of factor Va proceeds via a biphasic reaction. The first step is a rapid cleavage at Arg$^{506}$ in the heavy chain domain of factor Va that results in the formation of a reaction intermediate with partial cofactor activity. This reaction intermediate is subsequently fully inactivated by slow cleavage at Arg$^{306}$. Protein S was found to stimulate the inactivation of membrane bound factor Va 10-fold by specific acceleration of the cleavage at Arg$^{306}$.

Factor Xa protects factor Va from inactivation by APC by blocking the cleavage site at Arg$^{506}$. The presence of factor Xa does not completely inhibit factor Va inactivation by APC, however. In the presence of saturating factor Xa concentrations, factor Va inactivation proceeds with a slow rate that is associated with APC-catalyzed cleavage at Arg$^{306}$ which is apparently not affected by factor Xa.

These conclusions are supported by immunoblot analysis. Immunoblots of time courses of inactivation of membrane-bound factor Va by APC, in which the heavy chain and its degradation products were visualized with an polyclonal antibody, showed transient generation of a reaction product with a MW of about 75,000, which is formed after rapid cleavage of the peptide bond at Arg$^{506}$ by APC. When protein S is present, there is less accumulation of the 75,000 dalton fragment and increased formation of products with molecular weights of about 45,000 and 30,000, which is indicative for accelerated processing of the 75,000 dalton intermediate by protein S dependent increase of the rate of cleavage at Arg$^{306}$. In the presence of factor Xa, there is no formation of the 75,000 dalton reaction intermediate. In this situation, products with MW of about 62,000/60,000 and 45,000 are formed which shows that factor Xa blocks cleavage at Arg$^{506}$ and that inactivation of factor Va proceeds via slow cleavage at Arg$^{306}$.

The determination of the effects of factor Xa and protein S on the peptide bond cleavages at Arg$^{506}$ and Arg$^{306}$, respectively, was confirmed by kinetic analysis of APC catalyzed inactivation of factor Va$^{R506Q}$. Protein S drastically stimulates inactivation of factor Va$^{R506Q}$ which is primarily associated with cleavage at Arg$^{306}$. Moreover, factor Xa does not protect factor Va$^{R506Q}$ from inactivation by APC. The latter observation is explained by the fact that factor Va$^{R506Q}$ lacks the target site for factor Xa.

The description contained herein marks the first time that a profound effect is reported for protein S in a reaction system with purified coagulation factors. Earlier publications by Bakker et al., *Eur. J. Biochem.* 208: 171–78 (1992), Solymoss et al., *J. Biol. Chem.* 263: 14884–90 (1988), and Tans et al., supra, described modest effects for protein S. According to the data reported here, however, cleavage at Arg$^{506}$ is barely affected by protein S. It turned out that protein S is actually required at a later stage of the inactivation process, that is when Arg$^{306}$ is cleaved. The presence of protein S ensures rapid conversion of a partially active reaction intermediate (factor Va cleaved at Arg$^{506}$) into a product with no detectable cofactor activity, an effect that may be of prime physiological importance.

According to the invention, various pharmaceutical preparations containing protein S or mutants of protein S can be tested according to the invention and employed for treating patients if the preparations increase APC response or correct APC resistance. The term "treating" in its various grammatical forms in relation to the present invention refers to preventing, curing, reversing, attenuating, alleviating, minimizing, suppressing or halting the deleterious effects of a disease state or progression.

Protein S mutants employed according to the invention can have various insertional and deletional changes made in the amino acid sequence. Additionally, mutants include proteins where various amino acid substitutions are undertaken. Preferably, only conservative amino acid alterations are preformed. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, mutants include variants and fragments of protein S, such as analogs, derivatives, muteins and mimetics of natural protein S that retain the ability to cause the beneficial results described herein. Fragments of the protein S refer to portions of the amino acid sequence of the protein S polypeptide that also retain this ability. The variants and fragments can be generated directly from protein S itself by chemical modification by proteolytic enzyme digestion, or by combinations thereof. Additionally, methods of synthesizing polypeptides directly from amino acid residues also exist.

Non-peptide compounds that mimic the binding and function of a protein ("mimetics") can be produced by the approach outlined in Saragovi et al., Science 253: 792–95 (1991). Mimetics are peptide-containing molecules which mimic elements of protein secondary structure. See, for example, Johnson et al.,"Peptide Turn Mimetics" in BIOTECHNOLOGY AND PHARMACY, Pezzuto et al., eds., (Chapman and Hall, 1993). The underlying rationale behind the use of peptide mimetics is that the peptide backbone of proteins exists chiefly to orient amino acid side chains in such a way as to facilitate molecular interactions For the purposes of the present invention, appropriate mimetics can be considered to be the equivalent of protein S itself.

Mutants, such as variants and fragments, can be created by recombinant techniques employing genomic or cDNA cloning methods. Site-specific and region-directed mutagenesis techniques can be employed. See 1 CURRENT PROTOCOLS IN MOLECULAR BIOLOGY, chapter 8, Ausubel et al., eds. (J. Wiley & Sons, 1989) and Supp. 1990–93; PROTEIN ENGINEERING, Oxender & Fox, eds. (A. Liss, Inc., 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit., and CURRENT PROTOCOLS IN MOLECULAR BIOLOGY, vols. 1 & 2, supra.

Although the protein S preparation according to the invention might further contain active ingredients like protein C, APC and/or other factors of fibrinolysis and anticoagulation, it surprisingly turned out that protein S itself is effective as a treatment for abnormal APC response or APC resistance. In a preferred embodiment of the invention, the protein S preparation does not contain factor V.

The protein S preparations according to the invention comprise pharmaceutically acceptable carriers. Pharmaceutically acceptable carriers include aqueous solutions, non-toxic excipients, including salts, preservatives, buffers and the like, as described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (7th ed.).

Surprisingly, some protein S preparations show different effects on the APC activity in factor $Va^{R506Q}$ inactivation. Protein S preparations that show the highest stimulation of the APC response according to the present invention will be best suited for treating patients. A functionally active protein S preparation enhances the APC activity even at very low concentration, for example at 50 nM protein S/25 nM APC.

The effectiveness of a protein S preparation for treating an abnormal APC response or APC resistance can be determined by:

$$\frac{\text{Factor } Va^{R506Q} \text{ inactivation}(+ \text{ protein } S \text{ after 10 min})}{\text{Factor } Va^{R506Q} \text{ inactivation}(- \text{ protein } S \text{ after 10 min})}$$

If the above ratio is in the range 0.001–0.5, preferably 0.001–0.3, at 50 nM protein S or protein S mutant, then the preparation is effective. The above ratio is based upon a comparison of APC activity after a 10-minute incubation in the presence and the absence of protein S (the level of inactivation can be based upon the amount of active factor $Va^{R506Q}$ remaining after incubation). If the protein S preparation is ineffective, the ratio will be 1:1. Quite surprisingly, a protein S preparation that enhances the APC activity on factor $Va^{R506Q}$ is most suitable for treating protein S deficiency or thrombotic and thromboembolic conditions in patients, generally.

Preferably, a protein S preparation increases APC response at least 10 fold. More preferably, the APC response is increased at least 25 fold.

A method of treating reduced APC response or APC resistance in a patient using protein S is effective only if the protein S preparation is capable of enhancing the APC activity on the factor $Va^{R506Q}$, which can be determined by the method according to the invention. The surprising differences in the protein S preparations might probably associated with a different extent of glycosylation, gamma-carboxylation, proteolytic processing or other post-translational modifications.

It is especially important to investigate the efficacy of protein S for treating APC response, when recombinant protein S or protein S mutants are determined for their functional action. For example, deletion mutants of protein S can be evaluated according to the invention in order to chose suitable dosages or regimens. These deletional mutants lack up to about ⅔ of the amino acids in the C-terminal region. It is also advantageous to assess the potency of a protein S preparation which is prepared from human or animal plasma, such as a preparation according to U.S. Pat. No. 5,254,532. When protein S preparations have undergone various physical and/or chemical treatments, such as treatment for viral inactivation, it still is recommended to prove whether the preparation remains effective.

The protein S preparation according to the U.S. Pat. No. 5,254,532, which has undergone a heat treatment for viral inactivation according to U.S. Pat. No. 4,640,834, is very efficacious for the treatment of an abnormal APC response. This preparation can be prepared from human plasma by various chromatographic methods, including ion exchange chromatography and immunoaffinity chromatography. According to PCT application WO 95/01433, moreover, protein S deletion mutant that is deficient in C4b-binding polypeptide is effective.

Patients who are heterozygous or homozygous for a Factor Va$^{R506Q}$ can be treated according to the present invention. Preferably, homozygous patients are treated because the clinical manifestations of homozygous patients are more severe. The need for treating these patients is especially great when other risk factors are present. The risk factors include protein S deficiency, pregnancy (including impending delivery), immobilization, acute or chronic inflammatory disorder, especially when there is an increased level of C4b binding protein. Additionally, with some disorders it is appropriate to counteract coagulation disorders caused by oral contraceptives.

The invention is further described by the following example, which are illustrative of the invention but do not limit the invention in any manner.

EXAMPLE 1

Cofactor activities of various protein S preparations (No. 1, 2 and 3)

A factor Va assay according to Tans et al., *Blood* 77: 2641–48 (1991), was modified to determine the effects of various protein S preparations on the inactivation of factor Va$^{R506Q}$. All preparations included purified protein S, but purified according to different procedures. The protein S was in a normal buffer (25 mM Hepes, 175 mM NaCl, pH 7.5). The molar concentrations were calculated from the protein concentration using a molecular weight of protein S of 70,000. Because this study was a blind study, the preparations were not further characterized.

The preparations included 25μM phospholipid (10/90 DOPS/DOPC), and were incubated with 3 mM calcium chloride, 0.4 nM factor Va$^{R506Q}$ (isolated from a patient who was homozygous for the mutation, using the method according to Nicolaes et al., *J. Biol. Chem.* 270: 21158–66 (1995)), 0.25 nM APC (produced by a method according to EP 0519903 A1) in the presence of the test preparations (50 nM protein S).

After the incubation, the inactivation of factor Va$^{R506Q}$ was subsequently measured in a prothrombinase system containing 50 μM phospholipid vesicles (10/90 DOPS/DOPC; M/M), 0.5 μM prothrombin, 5 nM factor Xa, 2 mM CaCl$_2$ and 0–50 μM factor Va-containing sample. After 1 minute, the amount of thrombin formed is measured with S2238 (Chromogenix). When in the inactivation system factor Va$^{R506Q}$ is incubated with APC with or without 50 nM protein S, the following ratio is determined:

$$\frac{\text{Factor Va}^{R506Q} \text{ inactivation}(+ \text{ protein } S \text{ after 10 min})}{\text{Factor Va}^{R506Q} \text{ inactivation}(- \text{ protein } S \text{ after 10 min})}$$

The ratios for three different protein S preparations were 0.11, 0.25, and 0.35 respectively. See FIG. 1. Other protein S preparations gave ratios of 1 to 1, and thus would not be useful for treating abnormal APC response (data not included).

EXAMPLE 2

Effects of protein S and factor Xa on APC catalyzed inactivation of membrane bound factor Va$^{R506Q}$ Purified human factor Va$^{R506Q}$ (0.55 nM) was incubated with 1 nM APC and 25 μM phospholipid vesicles (DOPS/DOPC, 10/90, M/M) in 25 mM Hepes (pH 7.5), 175 mM NaCl, 3 mM CaCl$_2$ and 6 mg/ml BSA at 37° C. in the absence (▲) or presence of 490 nM protein S (■) or 20 nM factor Xa(●). At the indicated time points factor Va activity was determined according to the above described method.

Compared with normal factor Va, the inactivation of factor Va$^{R506Q}$ is slow and monophasic because no cleavage occurs at position 506 due to the mutation. The time course of factor Va$^{R506Q}$ inactivation can be fitted with a single exponential equation derived for an inactivation reaction in which factor Va is converted via a single peptide bond cleavage ($k_{306}$=1.7×10$^6$ M$^{-1}$ s$^{-1}$) into a reaction product that lacks factor Va cofactor activity.

The data show that the inactivation of factor Va$^{R506Q}$ was not affected by factor Xa and that protein S accelerated inactivation 12 fold ($k_{306}$=2.0×10$^7$ M$^{-1}$ s$^{-1}$).

It was observed that protein S drastically stimulates inactivation of factor Va$^{R506Q}$ which is primarily associated with cleavage at Arg$^{306}$ and that factor Xa does not protect factor Va$^{R506Q}$ from inactivation by APC. The latter observation is explained by the fact that factor Va$^{R506Q}$ lacks the target site for factor Xa.

It is to be understood that the description, specific examples and data, while indicating preferred embodiments, are given by way of illustration and exemplification and are not intended to limit the present invention. Various changes and modifications within the present invention will become apparent to the skilled artisan from the discussion and disclosure contained herein.

What is claimed is:

1. A method for evaluating the effect of a protein S pharmaceutical preparation on APC response, comprising the steps of:
    (a) incubating the Protein S pharmaceutical preparation with factor Va$^{R506Q}$ and APC;
    (b) determining a level of factor Va$^{R506Q}$ inactivation in the presence of the protein S pharmaceutical preparation; and
    (c) comparing the level of step (b) with a level of factor Va$^{R506Q}$ inactivation obtained in the absence of the protein S pharmaceutical Preparation in order to evaluate the effect of the protein S pharmaceutical preparation.

2. A method according to claim 1, wherein during step (a) the protein S pharmaceutical preparation is contacted with calcium ions and phospholipids.

3. A method according to claim 1, wherein the protein S pharmaceutical preparation contains at least one compound selected from the group consisting of protein S or a mutant of protein S.

4. A method according to claim 1, wherein the protein S pharmaceutical preparation is a plasma sample.

5. A method according to claim 1, wherein the factor Va$^{R506Q}$ is obtained from plasma or a plasma fraction.

6. A method according to claim 1, wherein the factor Va$^{R506Q}$ is recombinant factor Va$^{R506Q}$.

7. A method according to claim 1, wherein the incubating step is performed at a temperature of about 15° C.–37° C. for about 5–30 minutes.

8. A method according to claim 7, wherein the level of inactivation is based upon measuring the amount of residual active factor Va$^{R506Q}$ remaining after the incubating step.

9. A method according to claim 8, wherein the amount of residual active factor Va$^{R506Q}$ can be determined by detecting cofactor activity for thrombin generation.

10. A method of treating a patient suffering from a reduced APC response, comprising the step of administering a pharmaceutical preparation comprising protein S or a mutant of protein S to said patient.

11. A method according to claim 10, wherein the patient suffers from APC resistance.

12. A method according to claim 11, wherein the patient is homozygous for a factor Va$^{R506Q}$ mutation.

13. A protein S pharmaceutical preparation for treating patients with reduced APC response, comprising (i) protein S or a mutant of protein S and (ii) phospholipids in a pharmaceutically acceptable carrier.

14. A composition according to claim 13, wherein the phospholipids are in a vesicle form.

15. A method according to claim 10, wherein phospholipids are administered along with the protein S or protein S mutant.

16. A method according to claim 15, wherein the phospholipids are in a vesicle form.

17. A method of treating a patient according to claim 10, wherein the protein S or protein S mutant is selected based upon its capability to inactivate factor Va$^{R506Q}$.

18. A method of treating a patient suffering from a reduced APC response, comprising:

selecting a protein S pharmaceutical preparation comprising protein S or a protein S mutant based upon its capability to inactivate factor Va$^{R506Q}$; and providing the patient with the protein S pharmaceutical preparation to treat the reduced APC response.

19. A method according to claim 1, wherein the protein S pharmaceutical preparation is a purified preparation.

20. A preparation according to claim 13, wherein the protein S pharmaceutical preparation is a purified preparation.

21. A method according to claim 18, wherein the protein S pharmaceutical preparation is a purified preparation.

* * * * *